_US005959102A_

United States Patent [19]
Wasserman et al.

[11] Patent Number: 5,959,102
[45] Date of Patent: Sep. 28, 1999

[54] STARCH PURIFICATION BY THERMALLY TOLERANT BROAD PH RANGE PROTEOLYTIC ENZYMES

[75] Inventors: Bruce Wasserman, Belle Mead; Chen Mu-Forster, Edison, both of N.J.

[73] Assignee: Rutgers University, Piscataway, N.J.

[21] Appl. No.: 08/886,169

[22] Filed: Jun. 30, 1997

[51] Int. Cl.$^6$ .................................................. C08B 30/04
[52] U.S. Cl. ............................. 536/128; 127/65; 127/67; 127/71; 435/275; 536/102; 536/124; 536/127
[58] Field of Search .................................. 127/34, 36, 38, 127/39, 40, 65, 71, 67; 536/102, 124, 127, 128; 435/275

[56] References Cited

U.S. PATENT DOCUMENTS

| | | | |
|---|---|---|---|
| 3,488,256 | 1/1970 | High et al. | 195/7 |
| 3,753,857 | 8/1973 | Rogols et al. | 195/7 |
| 5,246,718 | 9/1993 | Haring et al. | 426/18 |

FOREIGN PATENT DOCUMENTS

| | | |
|---|---|---|
| 350 613 B1 | 10/1993 | European Pat. Off. . |
| 139361 | 12/1979 | Germany . |
| 04079891 | 3/1992 | Japan . |

OTHER PUBLICATIONS

Mu et al., "Heat–Induced Fragmentation of the Maize Waxy Protein During Protein Extraction from Starch Gransules." 1998.
*Cereal Chem.*, vol. 75 (4): 480–483.
Mu—Forster et al., "Surface Localization of Zein Storage Proteins in Starch Granules from Maize Endosperm. Proteolytic Removal by Thermolysin and in vitro Crosslinking of Gramule–Associated Polypeptides", *Plant Physiol.*, vol. (4):1563–1571, 1998.
Rahman et al., "The Major Proteins of Wheat Endosperm Starch Granules." *Aust. J. Plant Physiol.*, 22(5): 793–803, 1995.
Harvey et al., "Hydrolysis of Endosperm Protein in *Zea Mays*". *Plant Physiol.*, vol. 53(3): 453–457, 1974.
Van Twisk, Pieter., "Hydrolyzed Starch Products from Corn Grits". *Stärke* (Starke), vol. 22 (7): 228–230, 1970.
Weegels et al. "Enzymes as a Processing Aid in the Wheat Starch Industry" America Assoc. of Cereal Chemists 74th Annual Meeting, Wash. D.C., Oct. 29–Nov. 2, 1989 Cereal Foods World 34(9):753, 1989.
Keil, B. "Specificity of Proteolysis", Springer–Verlag, Berlin, Heidelberg, pp. 155–156, (1992).
K. Cline, et al., "Thermolysin Is a Suitable Protease for Probing the Surface of Intact Pea Chloroplasts", Plant Physiol. (1984), vol. 75, pp. 675–678.
S.R. Eckhoff, et al., "Starch Recovery from Steeped Corn Grits as Affected by Drying Temperature and Added Commercial Protease", Cereal Chem. vol. 68, No. 3, 1991, pp. 319–320.
J. Feder, et al., "Studies on the Role of Calcium in Thermolysin", Biochemistry, vol. 10, No. 24, 1971, pp. 4552–4555.

B.R. Hamaker, et al., "Efficient Procedure for Extracting Maize and Sorghum Kernel Proteins Reveals Higher Prolamin . . . " Cereal Chem. vol. 72, No. 6, 1995, pp. 583–588.
R.C. Hoseney, "Proteins of Cereals", Principles of Cereal Science and Technology, Ch. 3, St, Paul, MN: American Association of Cereal Chemists, 1994, Ed. 2, pp. 65–79.
R.C. Hoseney, "Wet Milling: Production of Starch, Oil and Protein", Chapter 7, Principles of Cereal Science and Technology, St. Paul, MH: American Association of Cereal Chemists, 1994, Ed. 2, pp. 147–157.
J.A. Kirihara, et al., "Differential expression of a gene for a methionine–rich storage protein in maize", Mol. Gen. Genet (1988) 211, pp. 477–484.
B.A. Larkins, et al., "The zein proteins of maize endosperm", (1984), Trends Biochem. Sci., 9:306–308.
J.B. May, "Wet Milling Process and Products", Chapter 12, Corn, Chemistry and Technology, 1987, American Association of Cereal Chemists, pp. 377–397.
Chen Mu, et al., "Association of a 76 kDa polypeptide with soluble starch synthase 1 activity in maize (cv B73) endosperm", The Plant Journal (1994), 6(2), pp. 151–159.
Ch. Mu–Forster, et al., "Physical Association of Starch Biosynthetic Enzymes with Starch Granules of Maize Endosperm" Plant Physiol. (1996), 111:821–829.
J.D. Steinke, et al., "Steeping Maize in the Presence of Mutiple Enzymes. I. Static Batchwise Steeping", Cereal Chem., vol. 68 No. 1, pp. 7–12, (1991).
J. D. Steinke, et al., "Steeping Maize in the Presence of Multiple Enzymes. II. Continuous Countercurrent Steeping", Cereal Chemistry, (1991), vol. 68, No. 1, pp. 12–17.
M. Tajima, et al., "Role of Calcium Ions in the Thermostability of Thermolysin and *Bacillus subtilis* var. *amylosaccharticus* Neutral Protease", E.J. Biochem., vol. 64, (1976), pp. 243–247.
C.M Wilson, "Proteins of the Kernel", Chapter 9, Corn, Chemistry and Technology, (1987), American Association of Cereal Chemists, pp. 273–310.
C.M. Wilson, "Multiple Zeins from Maize Endosperms Characterized by Reversed–Phase High Performance Liquid Chromatography", Plant Physiol. (1991), vol. 95, pp. 777–786.
Q. Xu, et al., "Organization of Photosystem I Polypeptides", Plant Physiol. (1995), vol. 108, pp. 1067–1075.

(List continued on next page.)

*Primary Examiner*—Howard C. Lee
*Attorney, Agent, or Firm*—Davidson, Davidson & Kappel, LLC

[57] ABSTRACT

The present invention is directed to purifying starch granules from starch-bearing crops, preferably maize, which include treating starch granules with a thermally tolerant, broad pH range proteolytic enzyme that is specific for surface-associated proteins. Also disclosed are purified starch granules which are substantially free of surface-associated proteins. Uses of the isolated starch granules are disclosed.

14 Claims, 10 Drawing Sheets

OTHER PUBLICATIONS

E.T. Donhowe, et al., "Isolation and Characterization of Oat Aleurone and Starchy Endosperm Protein Bodies", Plant Physiol. (1983), vol. 71, pp. 519–523.

M. Kreis, et al., "Structure and Evolution of Seed Storage Proteins and Their Genes with Particular Reference . . . Rye", Oxford Surveys of Plant Molecular & Cell Biology, vol. 2, (1985), pp. 253–317.

M.A. Shotwell, et al., "The Biochemistry and Molecular Biology of Seed Storage Proteins", The Biochemistry of Plants vol. 15, (1989), pp. 297–345.

C.R. Lending, et al, "Immunolocalization of avenin and globulin storage proteins in developing endosperm of *Avena sativa* L.", Planta (1989), vol. 178, pp. 315–324.

J.H. Skerritt, et al., "Specificity, characteristics of monoclonal antibodies to wheat grain storage proteins", Biochimica et Biophysica Acta (1986), vol. 874, pp. 245–254.

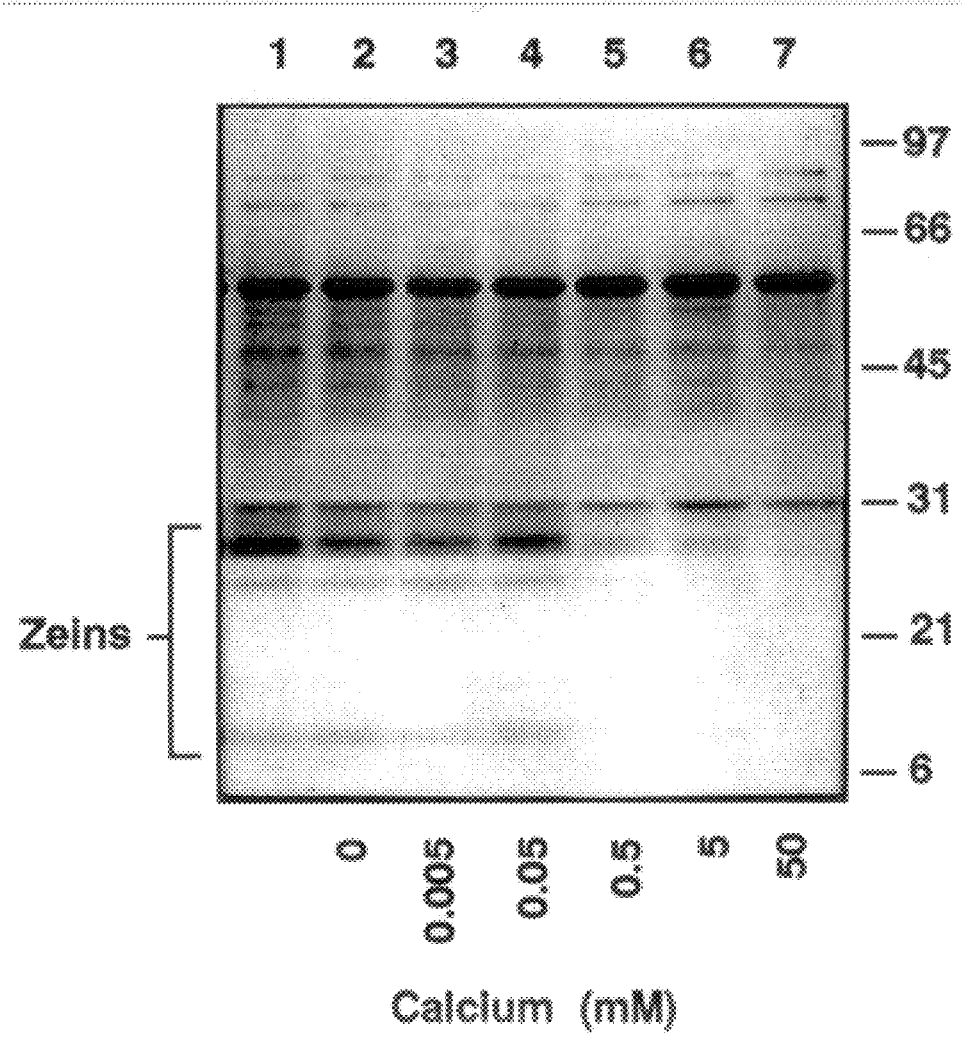

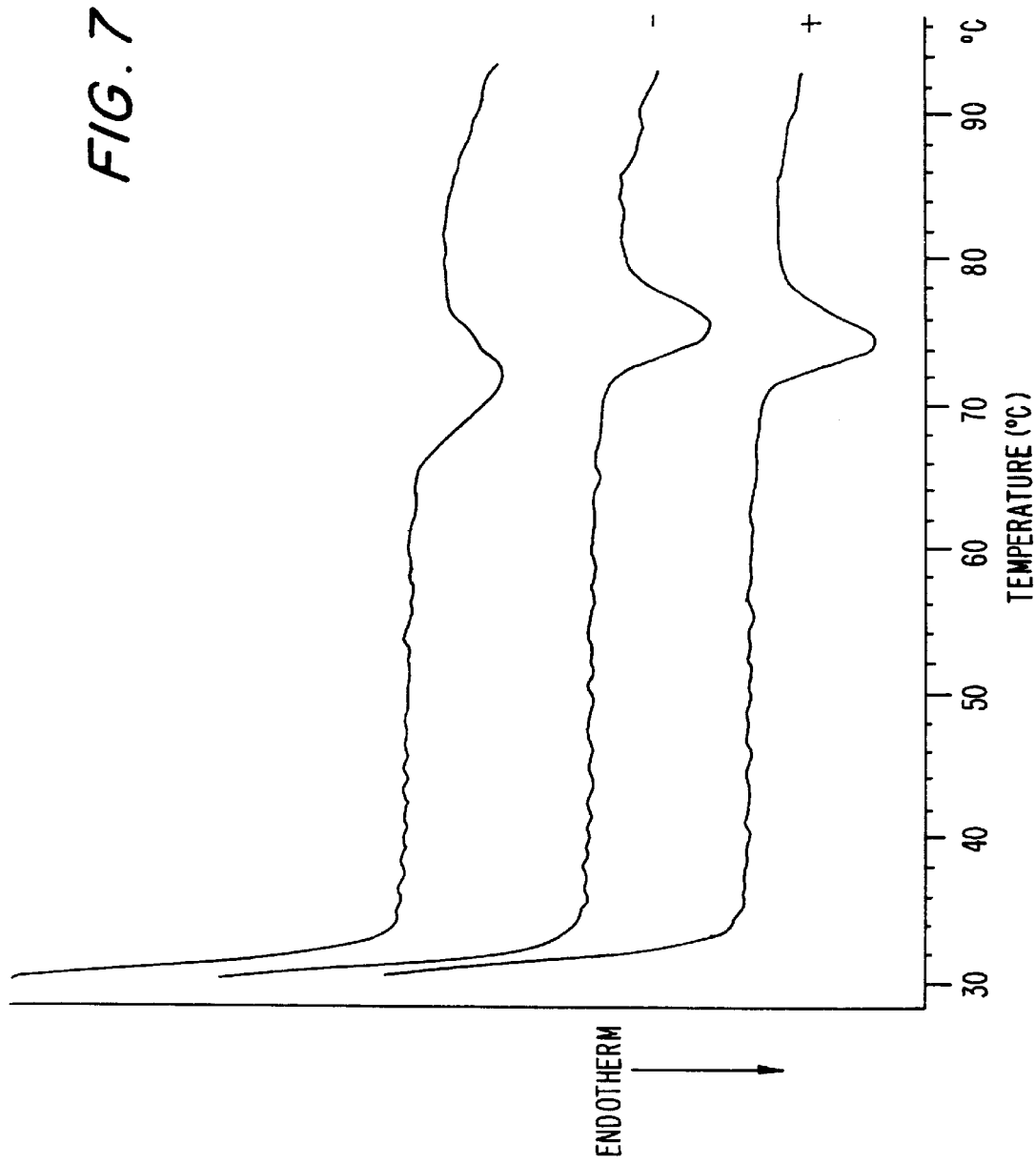

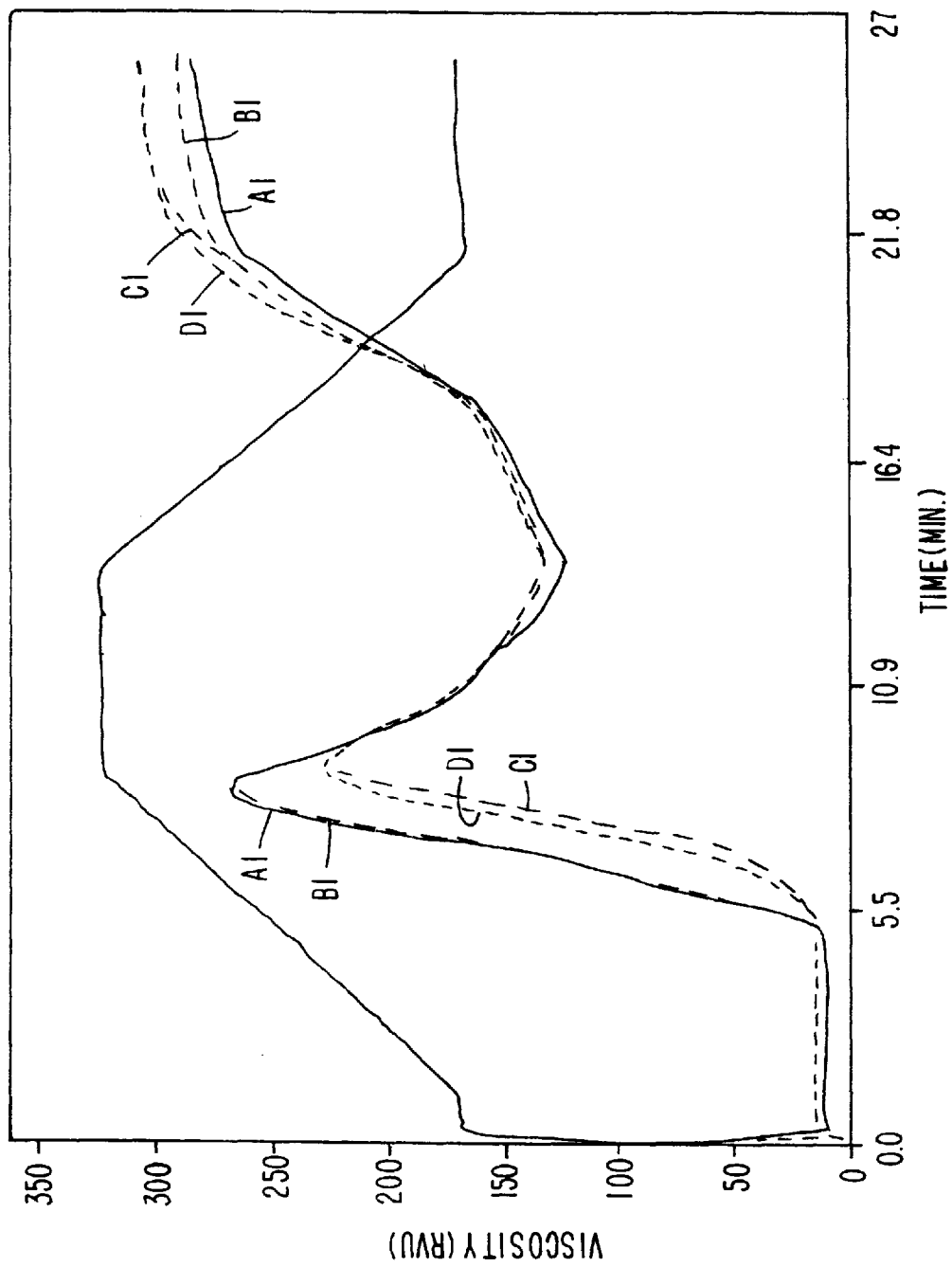

MAAKMLALFALLALLALCASASATSATHIPGHLPPVMPLGTMNPCMQYCMMQQGLASLMACPS

LMLQQLLALPLQTMPVMMPQMMTPNMMSPLMMPSMMSPMBLPSMMSQMMMPQCHCDAV

SQIMLQQQLPFMFNPMAMTIPPMFLQQPFVGAAF

STARCH PURIFICATION BY THERMALLY TOLERANT BROAD PH RANGE PROTEOLYTIC ENZYMES

This invention was made in part with United States Government support under the United States Department of Agriculture (U.S.D.A.) National Research Initiative (95-02531) and the United States Government may have certain rights in this invention.

FIELD OF THE INVENTION

The invention is directed to improved methods for producing high quality, purified starch from starch-bearing crops. In particular, the invention is directed to the enzymatic removal of surface-associated protein contaminants from starch granules using thermally tolerant, broad pH range proteolytic enzymes.

BACKGROUND OF THE INVENTION

Maize (also known as corn in North America), is a major source of refined starch, i.e., cornstarch. Starch is produced from maize and other starch-bearing crops by either dry milling or wet milling. It is extracted from the endosperm component of the maize kernel, which is composed of individual starch granules embedded in a proteinaceous matrix. Thus, starch purification requires separation of the starch from the protein component.

Starch quality is strongly associated with purity, i.e., freedom from undesirable contaminants such as proteins or lipids, and starch production efforts are often assessed by measurement of the protein or lipid content of purified samples (Hoseney, 1994).

Thus, an integral goal of a starch purification process is to produce a protein- and lipid-free product (Hoseney, 1994). The purification process allows for the disassociation of residual protein and lipid from resultant starch granules that can interfere with thermal and pasting properties and can impart an unpleasant taste to the starch. During the starch purification process, protein and lipid contaminants have been known to non-covalently adsorb off-flavors and pigments, thereby limiting some applications of the starch. Protein levels, may be used as a crude measure of starch purity (Eckhoff and Tso, 1991; Steinke and Johnson, 1991; Steinke et al., 1991) and are generally determined by measuring nitrogen using Kjeldahl assays (American Association of Cereal Chemists, 1983).

In order to provide highly refined starch, additional separation processes beyond wet or dry milling may be applied to separate the starch from the remaining surrounding proteins. For example, heretofore, a common means for reducing starch granule pigmentation and flavor has been extraction with organic solvents.

Wet milling refining processes are preferred because they provide more highly refined products than do dry milling refining processes, but wet milling is more costly than dry milling. Wet milling involves steeping corn kernels in a dilute aqueous solution of sulfur dioxide under controlled conditions of time, temperature, and lactic acid concentration. These conditions are necessary to soften the kernels, inhibit growth of microorganisms, and to cleave disulfide linkages of the protein matrix in which the starch granules are embedded, to facilitate the release of starch from proteins. The steep water is then collected and concentrated in order to recover soluble components. The softened maize is then further processed by a series of grinding and separating operations to separate the kernel into its components, the germ, hull and endosperm.

Efforts have previously been made to apply protease enzymes to reduce the steeping time and facilitate the starch wet milling process. Multiple enzymes (Eckhoff and Tso, 1991; Steinke and Johnson, 1991; Steinke et al., 1991) have been reported to shorten steeping time. For example, Steinke and Johnson, 1991, and Steinke et al. 1991, combined enzymes from *Aspergillis niger* (enzyme mixture was reported to include: cellulase, hemicellulase, beta-glucanase, pectinase and bromelin) with sulfur dioxide, in both batch and countercurrent processing, respectively, and reported shortened steeping times.

However, Steinke and Johnson, report that the amount of enzyme mixture required to conduct the process renders the process uneconomical considering that the process needs to be run at about 50° C., for up to 24 hours.

Haring et al., in U.S. Pat. No. 5,246,718, contemplates methods for improving the flavor of starch, especially hydrolyzed starch or gelling starch that is essentially gluten free. However, the gelling starch contains a significant amount of oligopeptides. The method described in Haring et al. includes incubating the starch with an enzymatically active peptidase, specifically, exo-peptidases obtained from food grade bacteria, to remove bitter taste from the starch. While this reference might arguably teach the removal of oligopeptides, having from 3 to 30 amino acids, there is no specific teaching in this reference suggesting removal of surface-associated or localized proteins from starch granules. In addition, the reference is devoid of any teaching suggesting removal of zein proteins using thermally tolerant, broad pH range proteolytic enzymes.

An enzymatic treatment of starch is known from East German patent 139 361. Described therein is a method for treating cereal starch containing insoluble gluten. However, it is not always desirable to enzymatically degrade gluten, which is a product of the maize milling process. In addition, the conventional enzyme based process previously utilized could not be employed for prolonged periods at the elevated temperatures generally utilized for starch processing, due to thermal denaturation of the enzymes.

A recent study (Mu-Forster et al., 1996) demonstrates that starch granule-associated proteins can be divided into two classes: internalized polypeptides and surface-associated polypeptides. This study further demonstrates that internalized proteins are not accessible to proteases unless these proteins are released from the starch granule by gelatinization.

The present invention reflects Applicants' observation that during the commercial wet milling process, proteins, particularly zeins, become associated with the surface of starch granules. These particular proteins comprise 62–74% of the protein content of maize endosperms (Hamaker et al., 1995; Wilson, 1987) and may serve to capture pigments and off-flavors.

Heretofore, there is no process for efficiently removing granule-associated proteins, namely those localized at the starch granule surface without gelatinizing the starch granules or degrading the gluten proteins in which the starch granules are embedded. The present invention provides a process for efficiently removing surface-associated proteins from the starch granule, thus yielding whiter starch having significantly less pigmentation. Consequently, the process of the present invention represents an alternative to the use of organic solvents for decolorizing maize starches.

An added feature of the present invention is that the process yields starch having a protein content from 0.13 to 0.14% compared to 0.4 to 1.0% normally found with conventional processes such as wet milling. As a result of the lower protein content, the starch appears whiter and is less prone to form or absorb off-flavors, which are drawbacks attending starch purified according to conventional processes.

The present invention reflects Applicants' endeavor to develop a process of purifying starch that is novel and attempts to address problems associated with conventional starch purification processes.

OBJECTS OF THE INVENTION

Accordingly, it is an object of the invention to provide improved and efficient methods for producing high quality starch from maize.

It is a further object of the invention to provide improved methods for removing contaminating proteins bound to starch granules during starch purification processes.

It is a further object of the invention to provide a method for removing surface-associated proteins from starch granules and leaving the starch granules intact.

It is a further object of the invention to provide a method for removing surface-associated proteins, particularly zeins from starch granules, thereby providing a significantly whiter and blander starch.

It is a further object of the invention to provide an improved method for producing high quality, purified starch products by incubating milled starch with a thermally tolerant, broad pH range proteolytic enzyme such as thermolysin.

It is a further object of the invention to provide a means to facilitate disengagement of starch granules from non-starch kernel components during steeping and post-steeping milling processes.

It is a further object of the invention to provide an improved method for producing high quality, purified starch having a significantly less protein and lipid content compared with commercial wet-milled starch.

SUMMARY OF THE INVENTION

In accordance with the above objects and others which will be apparent from the further reading of the specification, and of the appended claims, the present invention is related to the surprising discovery that surface-associated proteins, primarily zein proteins, coat the surfaces of starch granules and are liberated during the milling process, and that these hydrophobic proteins impact starch pigmentation, flavor and starch functionality.

The present invention is further related to the surprising discovery that the selective enzymatic removal of surface-associated starch granule proteins at elevated but sub-gelatinization temperatures, provides for an efficient and improved method for producing high quality, purified starch product.

The present invention is further related to the surprising and unexpected discovery that a thermally tolerant, broad pH range protease such as thermolysin selectively and effectively removes the surface-associated proteins from starch granules at sub-gelatinization temperatures.

According to an embodiment of the invention, there is provided a method for purifying starch obtained from starch-bearing crops which include treating starch granules with a thermally tolerant, broad pH range protease, preferably thermolysin, at a sub-gelatinization temperature to selectively remove surface-associated proteins from the surface of the starch granules. Suitable starch-bearing crops are well known in the art and include, but are not limited to maize, sorghum, wheat, barley, oats, rice, rye, potato, cassava, sweet potato, millet and banana. It is preferred that the step of treating the starch granules with the thermally tolerant, broad pH range protease be carried out at a sub-gelatinization temperature of from about 20° C. to about 68° C. The upper limit of the sub-gelatinization temperature may vary with starch-bearing crops other than maize.

According to another embodiment of the invention, there is provided a method for removing internalized proteins from starch granules obtained from starch-bearing crops which includes treating the starch granules with a thermally tolerant, broad pH range protease, preferably thermolysin at a gelatinization temperature sufficient to remove the internalized proteins from the starch granules. Suitable starch-bearing crops include but are not limited to maize, sorghum, wheat, barley, oats, rice, rye, potato, cassava, sweet potato, millet and banana. Preferably, the starch-bearing crop is maize.

According to another embodiment of the invention, there is provided a method for purifying starch obtained from maize which includes treating starch granules which have surface-associated proteins with a thermally tolerant, broad pH range protease, preferably thermolysin at a sub-gelatinization temperature to selectively remove the surface-associated proteins from the surface of the starch granules. It is preferred that the step of treating the starch granules with a thermally tolerant, broad pH range protease be carried out at a sub-gelatinization temperature of from about 20° C. to about 68° C. The treatment of the starch granules with a thermally tolerant, broad pH range protease is preferably conducted at a pH of about 2 to about 11.

In another preferred embodiment, the surface-associated proteins removed from the surface of the starch granules are zeins, having a molecular weight of about 10 to about 30 kDa as measured by SDS-PAGE.

In another preferred embodiment, the step of treating the starch granules with thermolysin is performed in a mixture containing calcium in a concentration of from about 0.5 mM to about 50 mM.

Another embodiment of the invention provides purified starch granules obtained from a starch-bearing crop which have been treated with a thermally tolerant, broad pH range protease and is substantially free of surface-associated proteins otherwise found on the starch granule. Suitable starch-bearing crops include but are not limited to maize, sorghum, wheat, barley, oats, rice, rye, potato, cassava, sweet potato, millet and banana. Preferably the starch-bearing crop is maize. It also preferred that the surface-associated proteins are zeins. Preferably the purified starch granules from starch-bearing crops are hypoallergenic and have an improved flavor relative to starch not treated with a thermally tolerant, broad pH range protease. Preferably the purified starch granules have reduced starch granule pigmentation relative to starch granules not treated with a thermally tolerant, broad pH range protease.

Another preferred embodiment of the invention provides for purified starch granules from maize having a protein content of from about 0.13 to about 0.14% relative to a protein content of 0.4 to 1.0% for starch not treated with a thermally tolerable, broad pH range protease.

Another embodiment of the invention provides for a starch product obtained from a process which includes treating the starch granules obtained from starch-bearing crops with a thermally tolerable, broad pH range protease at a sub-gelatinization temperature to selectively remove surface-associated proteins from the surface of the starch granules. Preferably the starch product is obtained from the above-mentioned process, wherein the suitable starch-bearing crops include but are not limited to maize, sorghum, wheat, barley, oats, rice, rye, potato, cassava, sweet potato, millet and banana. Preferably the starch product is obtained from maize.

A final embodiment of the present invention provides for a method of reducing pigmentation of starch from maize which includes treating maize during steeping or post-steeping processes or isolated starch granules with thermolysin to selectively remove surface-associated proteins from the surface of said starch granules. Preferably the surface-associated proteins removed from the surface of said starch granules are zeins.

The above, and other objects, features and advantages of the present invention will become apparent from the following description read in conjunction with the accompanying figures, in which like reference numerals designate the same elements.

BRIEF DESCRIPTION OF THE FIGURES

The following figures are illustrative of embodiments of the invention and are not meant to limit the scope of the invention as encompassed by the claims.

FIG. 6 Effect of Calcium on Zein Hydrolysis. Wet-milled starch granules were incubated with thermolysin at the Ca$^{2+}$ levels indicated. Proteins remaining associated with the starch granules were then extracted and analyzed by SDS-PAGE. Lane 1 contains a control with no thermolysin added. M denotes molecular mass markers.

FIG. 7 Differential Scanning Calorimetry Thermograms. Wet-milled starch granules were incubated in the absence (−) or presence (+) of thermolysin, and were analyzed by DSC as described under Materials and Methods.

FIG. 8 Viscoamylograph Viscosity Profiles of Thermolysin Treated Starch. Wet-milled starch granules were incubated in the absence (A,C) or presence (B,D) of thermolysin at 64° C. (C, D) and 50° C. (A, B) for 4 hours, and were subjected to RVA analysis.

DETAILED DESCRIPTION

Figure 1:
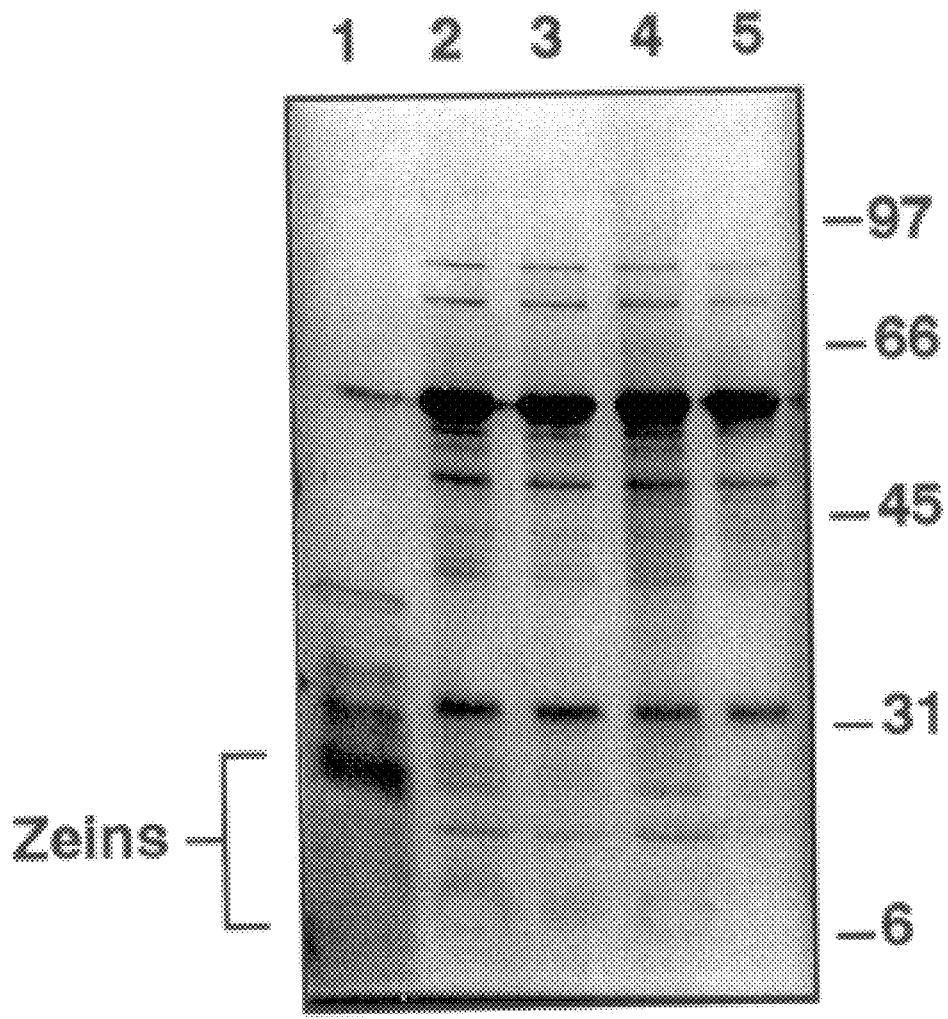
FIG. 1 Thermolysin-Catalyzed Removal of Proteins from Starch Granules. Starch granules isolated from B73 maize endosperm were incubated with thermolysin (2 μg/mg) as described in Materials and Methods at 64° C. for 30 min (lanes 2 and 3) or overnight (lanes 4 and 5). Following extensive washing, remaining proteins were extracted, analyzed by SDS-PAGE, and visualized by double-staining with Coomassie blue and silver. Each incubation was conducted in the absence (lanes 2 and 4) or presence (lane 3 and 5) of thermolysin, as indicated. In lane 1, proteins were first extracted from an equivalent quantity of gelatinized starch and were then incubated with thermolysin for 30 minutes.

The present invention provides improved methods for the production of high quality starch from maize by the efficient, selective removal of surface-associated proteins, and particularly surface-associated proteins such as zein proteins, from the surface of starch granules released during milling of maize.

Investigation of surface-associated proteins on the starch granules of milled maize has surprisingly demonstrated that surface-associated proteins, such as zein proteins, coat the surfaces of starch granules upon kernel disruption or homogenization, and that these hydrophobic proteins impact starch pigmentation. Zeins are seed storage proteins present in protein bodies in the endosperm of maize (Hoseney, 1994). Such storage proteins provide a source of nutrients to developing seedlings (Shotwell and Larkins, 1989).

In particular, the surfaces of commercially-produced wet-milled starch granules contain significant deposits of zein polypeptides. Since starch granules produced from amyloplasts by gentle mechanical release contain markedly reduced levels of zein (FIG. 3), it is possible that the binding of zeins to the granule surface occurs during the steeping and milling process where protein bodies and amyloplast membranes are destroyed and mixing of these components occurs. Irrespective of how zeins reach the surface of the starch granules, zeins comprise approximately 62–74% of the total protein content of maize endosperms (Hamaker et al. 1995), are hydrophobic and may serve to capture pigments and off-flavors, which in turn, imparts undesirable functionality.

It has also been surprisingly determined that it is possible to selectively remove the surface-associated zeins from such starch granules by enzymatic treatment that results in starches of significantly enhanced functionality.

Other surface-associated proteins present on starch granules of starch-bearing crops other than maize, particularly seed storage proteins that can be extracted by the method provided by the present invention include but are not limited to gliadin from wheat; secalin from rye; hordein from barley; kafirin from sorghum; avenin from oats; and oryzenin from rice. Support from the above becomes evident when considering that these seed storage proteins are similar in structure and amino acid composition to that of zeins. These properties include the feature that zeins and most of the above exemplified storage proteins can be extracted by 70% ethanol and they each share a high content of hydrophobic amino acids such as leucine, isoleucine, alanine, phenylalanine, valine and methionine (Hoseney et al. 1994; Shotwell and Larkins, 1989; Larkins et al. 1984; and Hamaker et al. 1995).

For example, Hamaker et al. (1995) disclose that the storage proteins zeins and kafarin bear a high degree of sequence homology to one another, are found in proteins bodies in the endosperm and are soluble in aqueous alcohol plus a reducing agent. In an additional example, Kreis et al. (1985) disclose that genes of storage proteins B1 hordein and one of the zein proteins also exhibit similar sequence homology.

In addition, it is to be understood that surface-associated proteins such as zeins and those occurring in other starch-bearing crops are generally associated with lipids, which are also removed concomitantly with the surface-associated proteins according to the present invention.

In accordance with one aspect of the present invention, wet-milled corn starch granules are treated with a thermally tolerant, broad pH range protease selective for zein proteins at sub-gelatinization temperatures which range from about 20° C. to about 68° C. In particular, it has been unexpectedly discovered that treatment with a thermally tolerant, broad pH range protease enables starch granules to be effectively treated for removal of surface-associated proteins, such as zeins, at starch processing temperatures. This method is also applicable to starch granules obtained from other suitable starch-bearing crops including but not limited to sorghum, wheat, barley, oats, rye, rice, potato, cassava, sweet potato, millet and banana. The treatment of starch granules with a thermally tolerant, broad pH range protease can be carried out during or after processing of starch-bearing crops and isolation of the granules. The various methods of processing starch and isolating starch granules from suitable starch-bearing crops is well-known to those skilled in the art.

Figures 9A, 9B:
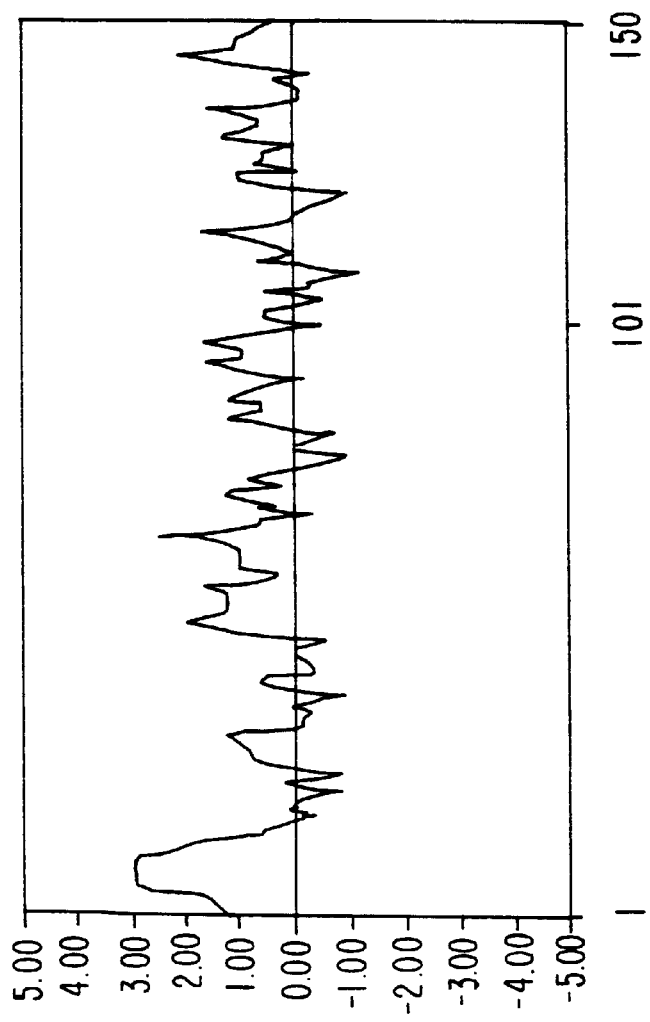
FIG. 9 Location of Thermolysin Recognition Sites on δ-Zein. A. Amino acid sequence. Double underlines denotes leucine and methionine rich thermolysin recognition sites (Kirihara et al., 1988). B. Hydropathy plot.

One preferred thermally tolerant, pH broad range protease is thermolysin, an art-known thermostable protease (a neutral metallo-endopeptidase) derived from *Bacillus thermoproteolyticus* which requires $Ca^{2+}$ to maintain thermal stability. Thermolysin is known to effectively act at protein-phospholipid/aqueous interfaces (Cline et al., 1984), although, to our knowledge, this is the first utilization of thermolysin at a protein-carbohydrate/aqueous interface. Thermolysin prefers substrates with bulky hydrophobic and aromatic residues (Iso, Leu, Val, Ala, Met, Phe) in the cleavage site. For example, the amino acid sequence of 10 kD δ-zein, a highly hydrophobic protein (Refer to FIGS. 9A and B; Kirihara et al., 1988; Keil, 1992) contains suitable recognition motifs for thermolysin proteolytic activity (letters with double underline). Other zeins share similar amino acid composition and structural properties. Thus, zeins are a class of proteins that are particularly suitable substrates for thermolysin. As stated above, other suitable proteins including but not limited to gliadin from wheat; secalin from rye; hordein from barley; kafirin from sorghum, avenin from oats; and orzyzenin from rice also contain a high content of hydrophobic amino acid residues. Thus, the above exemplified proteins and other proteins found in other starch-bearing crops which contain suitable recognition motifs for thermolysin proteolytic activity can also be effectively removed from the surface of starch granules.

Use of the metallo-endopeptidase thermolysin in the processes of the present invention has specific advantages, for example, reactions can be abruptly terminated by addition of EDTA to chelate $Ca^{2+}$, thus reaction times can be carefully controlled (Mu-Forster et al. 1996). Modulation of this reaction by manipulation of the ratio of $Ca^{2+}$ and chelators, however, is subject to the hardness level of water used for the process. In addition, the artisan will appreciate that thermolysin activity can also be optionally enhanced by supplementation with other proteases, e.g., thermally tolerant, broad pH range proteases.

The active pH range of thermolysin is compatible with steeping conditions. The term "steeping" is well-understood by those skilled in the art. Generally, the term encompasses submerging corn in water containing 0.1–0.2% sulfur dioxide at about 50–55° C. for 30–50 hours, to soften the kernels, inhibit growth of microorganisms, remove solubles and facilitate the release of starch from the protein matrix of corns (Hoseney, 1994; Eckhoff and Tso, 1991). In the early phase of the steeping process, the pH of the kernel is substantially higher than the steeping solution (pH 3–5), with equilibrium requiring about 15–18 hours (Biss and Cogan, 1996). However, it is known that the quality of starch purified from maize steeped at pH 5.0 is essentially identical to starch held at pH 3.5 (Biss and Cogan, 1996). Thermolysin, is active at a pH value of at least 2.0, and can be used under most steeping conditions. Proteins localized at the surface of starch granules from maize or other suitable starch-bearing crops are preferably extracted, wherein the treatment of the starch granules with a thermally tolerant, broad pH range protease is carried out at a pH of about 2 to about 11.

The amount of enzyme required to practice the invention is determined by electrophoretic analysis of the end product, and would generally encompass an amount that effectively removes zeins or other suitable proteins from the surface of the granule. In maize, this can be confirmed by determining the protein content of the resulting purified starch granules wherein the residual protein content is 0.13 to 0.14% relative to a protein content of 0.4% to 1.0% for starch not treated with a thermally tolerant, broad pH range protease.

In a preferred embodiment, the purification of starch from maize, according to the present invention, is conducted by wet milling, as conventionally carried out, with the improvement comprising the digestion of starch granule surfaces during the final wash steps that are used to cleanse the final starch product. This is preferably conducted by using static washers, which lengthen the process, but have the advantage of avoiding extensive requirements for new capital equipment.

An alternative embodiment contemplates promoting protein disengagement from starch granules during milling by genetically engineering a gene for the expression of the thermolysin enzyme into the endosperm of maize or other starch-bearing crop, either by means of a suitable vector capable of expressing active thermolysin in endosperm host cells, for localized insertion into endosperm tissues or by creating a transgenic strain of maize or other starch-bearing crop capable of expressing thermolysin in endosperm tissues. Thermolysin so expressed will remain inactive until exposed to steeping conditions, when $Ca^{2+}$ is added at elevated temperatures. A skilled artisan would know the technique required for producing the transgenic plant having incorporated into its genome a gene encoding thermolysin, wherein the thermolysin is activated during the milling process upon addition of $Ca^{2+}$.

In accordance with another aspect of the present invention, starch granules from suitable starch-bearing crops are treated with a thermally tolerant, broad pH range protease, preferably thermolysin at a gelatinization temperature sufficient to remove internalized protein from the starch granule. Gelatinization of starch granules is preferably carried out at a temperature of at least 69° C. The skilled artisan will appreciate that the temperature depends on whether it is desired to make the starch granules porous or to completely gelatinize the granule.

Starch granule-associated protein in maize can be divided into two categories: (1) internalized proteins tightly-associated with starch granules that become accessible to protease digestion only after starch is gelatinized, and (2) protease accessible proteins located at the starch granule surface. In the examples provided hereinbelow, starch granules from maize are proteolyzed at sub-gelatinization temperatures utilizing a thermally tolerant, broad pH range protease in order to identify and selectively remove surface-associated proteins.

In addition, as demonstrated by the examples provided hereinbelow, removal of zeins from starch granule surfaces by the processes of the present invention has a significant impact upon starch functionality and quality. Thermolysin deproteinized starch is significantly whiter, thus confirming the removal of undesirable pigmentation. Further, the removal of surface-associated proteins such as zeins results in the removal of objectionable flavors from starch yielding a blander starch, which in turn, produces a starch having an improved flavor. This characteristic of starch is highly desirable especially of starch that is incorporated into food products. (Haring et al., U.S. Pat. No. 5,246,718, incorporated by reference herein).

The present invention is now described, by way of examples illustrating various aspects of the present invention. They are not to be construed to limit the claims in any manner whatsoever.

The term "steeping" is well-understood by those skilled in the art. Generally, the term encompasses submerging corn in water containing 0.1–0.2% sulfur dioxide at about 50–55° C. for 30–50 hours, to soften the kernels, inhibit growth of microorganisms, remove solubles and facilitate the release of starch from the protein matrix of corn (Hoseney, 1994; Eckhoff and Tso, 1991).

The term "thermolysin" is meant to encompass other thermally tolerant, broad pH range proteases which are known to those skilled in the art and which will selectively remove surface-associated proteins from starch granules at a sub-gelatinization temperature.

The term "broad pH range" is generally meant to encompass a pH of about 2 to about 11.

The term "subgelatinization temperatures" is well-understood in the art. Generally, the term encompasses temperatures wherein starch granules remain intact and are not gelatinized.

The term "gelatinization temperatures" is well-understood in the art. Generally the term encompasses temperatures wherein starch granules become porous or gelatinize.

The term "internalized proteins" is meant to encompass granule-associated proteins that are not accessible to proteolytic attack unless the starch granules are made porous or gelatinized at a gelatinization temperature.

The term "surface-associated proteins" is meant to encompass proteins localized at the surface of the starch granules which are non-covalently or covalently bound to the surface of the starch granule.

The term "zeins" encompasses surface-associated proteins present on the starch granules of maize or zeins localized in protein bodies from maize, having a molecular weight ranging from about 10 to about 30 kDa as measured by SDS-PAGE.

The term "substantially free of surface-associated proteins" as applied to purified starch granules is meant to encompass the removal of 90 to 100% of surface-associated proteins from starch granules.

The term "hypoallergenic" is well understood in the art. Generally the term encompasses preparations that are less likely to cause an allergic reaction than other comparable preparations, i.e. cosmetics, lotion, foods, etc. As applied to the present invention it is meant to encompass starch granules that as a result of protein removal by the method of the present invention are less likely to cause an allergic reaction than starch granules wherein the protein is not removed.

Sources of Starch

Any suitable starch-bearing crop as exemplified above in the present invention can be employed in the processes according to the invention. Simply by way of example, kernels of maize (*Zea maize,* inbred line B73) were collected from ears of greenhouse-grown plants at 18–21 DAP, frozen in liquid $N_2$, and stored at –80° C. Industrial wet-milled starch inbred line W64 suspended in steeping solution was provided by Cerestar (Hammond, Ind.). Unless otherwise indicated, steeping solution was removed by repeated aqueous washing, and washed granules were air dried. Several examples (FIGS. 1, 3 and 5) utilized laboratory isolated granules prepared from maize cultivar B73 as described (Mu-Forster et al. 1996). A polyclonal antibody recognizing maize δ-zein (10 kDa) was a generous gift from Dr. Joachim Messing (Rutgers University, New Brunswick, N.J.). Thermolysin (protease type X from *Bacillus thermoproteolyticus;* EC 3.4.24.4) was obtained from Sigma Chemical Co., St. Louis, Mo.

Starch Granule and Amyloplast Isolation

Starch granules were isolated by low-speed centrifugation as described (Mu et al. 1994; Mu-Forster et al. 1996). Amyloplasts were isolated from B73 endosperm by gentle mechanical release as previously described (Denyer et al. 1996), with bovine serum albumin omitted from the amyloplast isolation medium. Ten grams of endosperms were obtained by hand dissection and were placed in a tilted Petri dish containing an amyloplast isolation medium consisting of buffer A (0.8 M sorbitol, 1 mM EDTA, 1 mM KCl, 2 mM $MgCl_2$, 2 mM DTT and 50 mM HEPES, pH 7.5) and incubated on ice for 30 minutes. A wide-bore pipette was used to slowly aspirate the cloudy liquid to a round-bottom centrifuge tube. Endosperms were re-immersed in buffer A, and sliced in half with a razor blade. The resultant extract was transferred to the centrifuge tube using a pipette with its tip covered with a piece of cheesecloth to filter out large particles. A yellow amyloplast-enriched pellet was recovered by centrifugation at 36×g for 10 minutes. The pellet was washed three times with buffer A and lysed in buffer B (10% glycerol, 10 mM EDTA, 1.25 mM DTT and 50 mM Tris/HCl, pH 7.0) containing 0.3% Triton X-100. A clear soluble fraction was recovered as amyloplast lysate by centrifugation at 15,000×g for 30 minutes, and was not further used in this study. Amyloplast-derived granule-bound proteins were then extracted with boiling the pellet for 15 minutes in 200 μl of SDS-PAGE sample buffer (3% SDS, 5% β-mercaptoethanol, 10% glycerol and 62.5 mM Tris/HCl, pH 6.9).

Protease Digestion of Starch Granules

Unless otherwise indicated, proteolytic digestion mixtures contained 50 mg (dry wt.) of isolated starch granules, 100 μg of thermolysin and 5 mM $CaCl_2$ in a volume of 1 ml. Unless otherwise indicated, hydrolysis was conducted at 64° C. for defined intervals as specified in each experiment, and reactions were terminated by addition of EDTA to 20 mM (Xu and Chitnis, 1995). Starch granules were centrifuged at 13,000×g for 5 minutes. Residual thermolysin was removed by five successive washings with water. Proteins were extracted as described below. Controls contained buffer in place of thermolysin.

Thermolysin digestion of proteins following their release from starch granules was conducted as follows: Starch granules (50 mg dry wt.) were boiled for 15 minutes in 1 ml of SDS-PAGE sample buffer. The solubilized protein were then digested by 100 μg of thermolysisn, and reactions proceeded as described above.

Protein Extraction and Analysis

Granule-associated proteins were recovered by extracting starch granules with SDS-PAGE sample buffer (20 μl of buffer per mg dry wt. of granule). Mixtures were then boiled for 15 minutes, cooled to room temperature, and were centrifuged at 13,000×g for 15 minutes. Extracted proteins were analyzed by SDS-PAGE using 9–18% gradient gels (Porzio and Pearson, 1976) and were visualized by double-staining with Coomassie blue and silver (Integrated Separation Systems, Hyde Park, Mass.) or by immunoblotting (below). Unless otherwise indicated, each lane was loaded with total protein extracted from 5 mg of isolated granules.

Immunoblotting was conducted as described (Harlow and Lane, 1988) with modifications. Proteins were electrophoretically transferred from SDS gels to nitrocellulose membranes (Schleicher and Schuell, Keene, N.H.) in 0.1% SDS, 100 mM glycine and 10 mM Tris/HCl, pH 8.0 (Towbin et al. 1979). The membranes were soaked for at least 1 hour in TBS-T buffer (0.15 M NaCl, 0.1% Tween- 20 and 10 mM Tris/HCl, pH 7.4) containing 1% BSA to block nonspecific binding sites. The membranes were then washed briefly with TBS-T once for 15 minutes and twice for 5 minutes at room temperature. Antiserum (30 ml, 1:10,000 dilution) was then added, and incubated for 1 hour with gentle shaking. Following three more washes with TBS, blots were incubated with horseradish peroxidase conjugated goat anti-rabbit IgG (Bio-Rad, Richmond, Calif.) at 1:6,000 dilution for 1 hour. Blots were then washed three times with TBS-T, and were visualized using enhanced chemiluminescence (ECL) (Amersham, Arlington Heights, Ill.).

Nitrogen content of the starch was determined using the improved Kjeldahl method (Method 46-11-A, AACC 1995). Protein content of starch granules was obtained by multiplying the percentage of nitrogen content by 5.7 (Tkachuk, 1969).

Color Measurement

Hunter color "L" (lightness), "a" (redness) and "b" (yellowness) values of starches were determined using a Minolta Chroma Reflectance Meter II (Abbey Chemical Agencies, Pymble, NSW, Australia) (Sicrede et al. 1990). Hue $H(°)_{ab}$ values were calculated as $tan^{-1}$="b"/ "a"($H(°)_{ab}$=0 for red, and $H(°)_{ab}$=90 for yellow). The instrument was standardized with a white plate (L=94,5, a=1.3, b=0.0). Samples were rotated at 45° C., and the eight measurements were then averaged.

Starch Thermal and Pasting Properties

For differential scanning calorimetry (DSC), dried wet-milled starch (4.8 ±0.1 mg) was weighed directly into tared aluminum DSC pans. Water was added to a starch-water ratio of 1:2, and total sample weights were determined after the pans were sealed. Samples were heated from 30° C. to 90° C. at a scan rate of 5° C./min in a differential scanning calorimeter. An empty DSC pan served as reference. Temperature of the onset of gelatinization (To), peak maximum temperature (Tm), and transition enthalpy (H) values were obtained. H values were calculated from peak areas and expressed as joules per g of dry matter. Pasting behavior of the starch samples was determined using a Rapid Visco-Analyzer (Newport Scientific, Narrabeen, Australia).

EXAMPLE 1

Thermolysin Treatment of Starch Granules
Removal of Low Molecular Weight Proteins from Granule Surfaces Isolated granules were subjected to thermolysin digestion at 64° C. for 30 minutes and overnight. Granule-associated proteins were visualized by SDS-PAGE (FIG. 1). Three sets of samples were analyzed. Controls were subjected to all wash steps, however, thermolysin was omitted (FIG. 1, lanes 2 and 4). A parallel set of samples consisted of granules subjected to thermolysin treatment (FIG. 1, lanes 3 and 5). Finally, to demonstrate that internalized granule polypeptides are thermolysin-sensitive following their removal from starch granules, a third set of sample was gelatinized in 2% SDS, and released internalized proteins were then treated with thermolysin just prior to SDS-PAGE (FIG. 1, lane 1).

FIG. 1 demonstrates that when the duration of granule hydrolysis is extended from 30 minutes to overnight, a series of lower molecular weight proteins (27, 22 and 10 kDa) are preferentially removed from the starch granule (FIG. 1, lane 5 vs. 4). In contrast, internalized proteins such as the 85-kDa SBEII (p85), the 76-kDa SSI (p76) and the 60-kDa waxy protein (p60) are resistant to thermolysin digestion (Mu-Forster et al. 1996). Upon addition of thermolysin following gelatinization of the starch matrix, each of these proteins was completely digested (FIG. 1, lane 1). This indicates that these internalized proteins are thermolysin-sensitive once they are removed from the starch granule matrix.

Analysis of residual nitrogen shows that thermolysin removed about 50% of total granule-associated protein (Table 1). The protein content of 0.13% to 0.14% achieved after thermolysin digestion is about half the levels measured in commercial wet-milled corn starch (0.3%) (Hoseney, 1994). This residual protein consists of intrinsically bound granule proteins which remain inaccessible to proteolytic digestion.

Table 1. Protein Content of Untreated and Deproteinized Maize Starches.

Wet-milled starch granules were incubated with thermolysin at concentration of 0.4 μg mg$^{-1}$ in 5 mM CaCl$_2$. Hydrolysis was conducted at 64° C. or 50° C. for 4 hours. Starch granules were washed five times with water to remove residual thermolysin and then air-dried. Control starch were treated parallel to deproteinized starch at each temperature with thermolysin omitted. Protein concentration of starch granule is expressed in percentage of weight of starch.

| Temperature (° C.) | Protein (%) Control Granules | Proteolyzed Granules | Reduction (%) |
|---|---|---|---|
| 50 | 0.33 ± 0.03 | 0.14 ± 0.02 | 58 ± 4 |
| 64 | 0.24 ± 0.03 | 0.13 ± 0.02 | 46 ± 5 |

Protein concentration values are the average of 3 measurements.

EXAMPLE 2

Selective Hydrolysis of Zein from Granule Surfaces

To establish whether the surface bound low molecular weight proteins that were removed were zeins (FIG. 1), immunoblotting studies were conducted using the antibodies raised against γ-16 or γ-27 kDa and δ-(10 kDa) zeins.

Figure 2A:
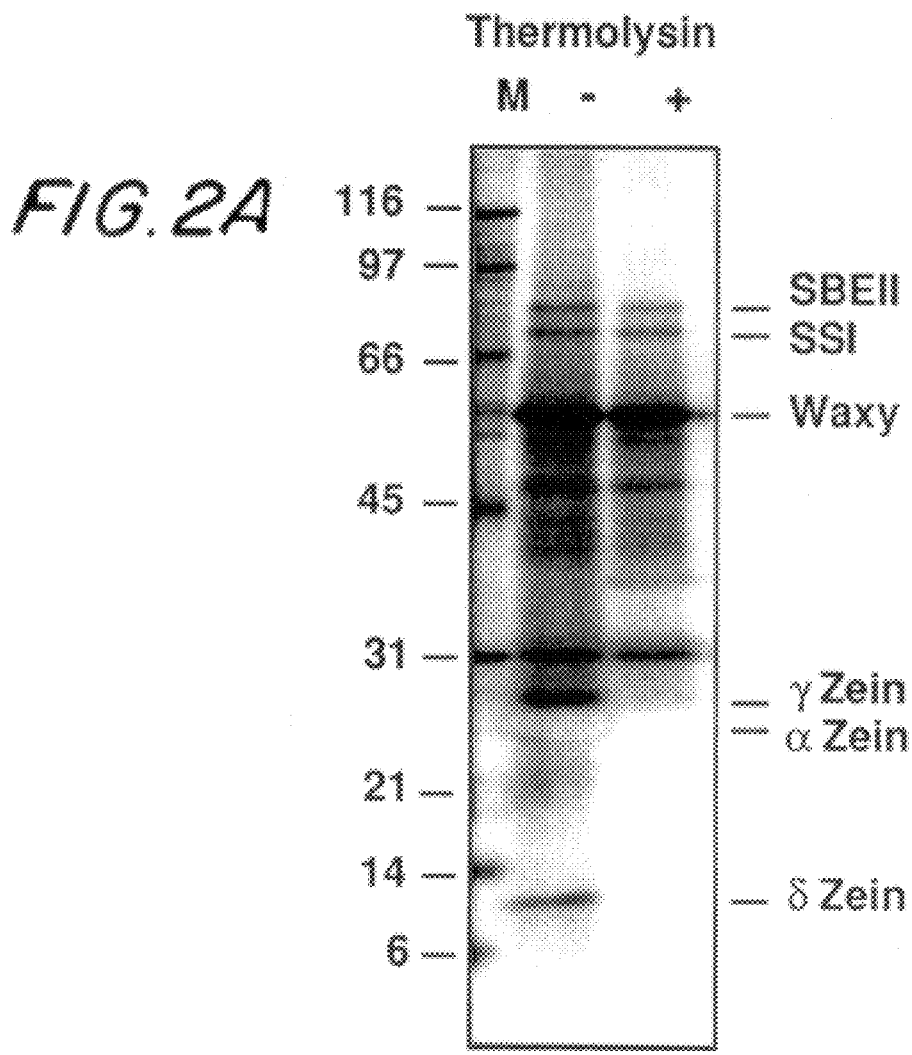
FIG. 2 Selective Hydrolysis of Zeins from Granule Surfaces. Wet-milled starch granules were incubated at 64° C. or 50° C. for 4 hr in the absence (−) or presence (+) of thermolysin as described in Materials and Methods. A, SDS-PAGE. B, Immunoblot probed with antibodies generated against the 10-kDa δ-zein. M denotes molecular mass markers.
Figure 2B:
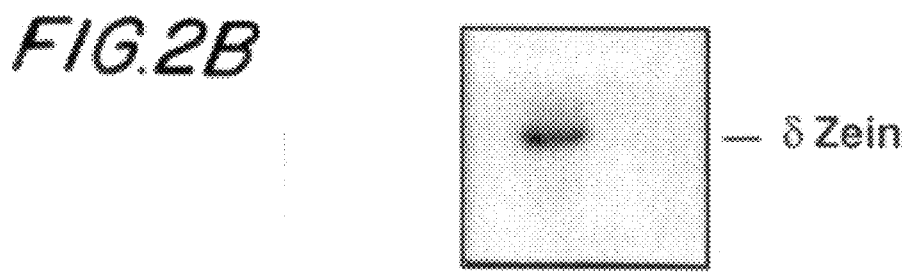

FIG. 2A shows that proteins ranging between 10 and 27 kDa were removed in their entirety. However, consistent with a previous study (Mu-Forster et al. 1996), proteins of larger molecular mass such as p85 (starch branching enzyme II), p76 (starch synthase I) and p60 (waxy protein) and p30 were not removed. SDS-PAGE profiles of proteins in the 10–30 kDa range are consistent with patterns characteristic of zeins documented in previous studies (FIG. 2A). An immunoblot directly demonstrates that γ-zein is selectively removed by thermolysin (FIG. 2B). Similar results were obtained with antibodies recognizing the γ-zein (16 or 27 kDa) (data not shown). These results clearly establish that digestion of starch granules with thermolysin selectively hydrolyzes zein proteins.

EXAMPLE 3

Origin of Granule-Associated Zein

There are two possible ways that zeins may associate with starch granules. First, if the zeins are located outside of the amyloplast, the association of zeins with starch granules would result from interactions of protein bodies with starch granules during kernel disruption. Alternatively, under normal growth conditions, zeins could be physically associated with starch granules within the amyloplast.

Figure 3:
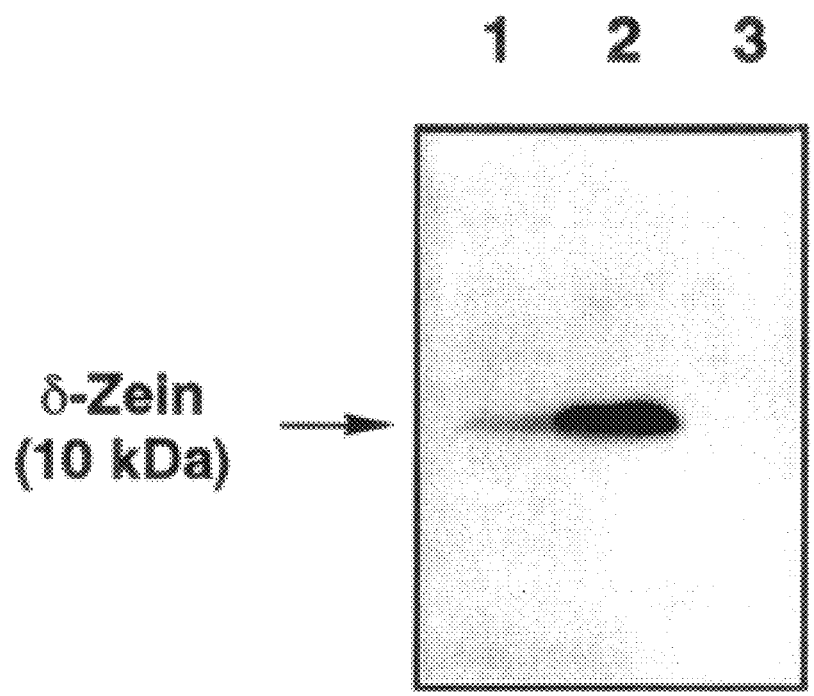
FIG. 3 Zein Content of Starch Granules Isolated from Amyloplasts and Homogenized Whole Endosperm. Immunoblot probed with antibodies generated against the 10-kDa δ-zein. Lane designations: 1. Protein extracted from 2.5 mg of starch isolated from purified amyloplasts of 15 DAP W64 maize. 2. Proteins extracted from 2.5 mg of starch isolated by homogenization from 15 DAP W64 whole endosperm. 3. Protein extracted from thermolysin digested starch from 15 DAP W64 endosperm.

If the first hypothesis is correct, then isolated amyloplasts should contain very little zein. To test this hypothesis, amyloplasts were purified from 13 DAP maize using a gentle mechanical release method and starch granules were then isolated from the amyloplasts. As a control, starch granules were also isolated by grinding the 13 DAP endosperm in buffer B using a mortar and pestle followed by low speed centrifugation and aqueous washes. Immunoblots probed using the 10-kDa zein antibody clearly show that starch granules from purified amyloplasts contained significantly less 10-kDa zein relative to starch granule proteins isolated from the 13 DAP maize endosperm (FIG. 3, lanes 1 vs. 2). This result demonstrates that in undisrupted kernels, the bulk of the 10-kDa zein is located outside of the amyloplast. The association of the zeins with the starch granules must therefore originate from protein bodies which are disrupted under the harsh conditions of kernel grinding and homogenization. The low level of zein associated with the amyloplast-derived starch is most likely due to a combination of binding that occurs during the amyloplast isolation procedure, and zein which associate with native granules.

EXAMPLE 4

Characterization of Zein Removal

Time Dependence of Zein Hydrolysis.

Figure 4:
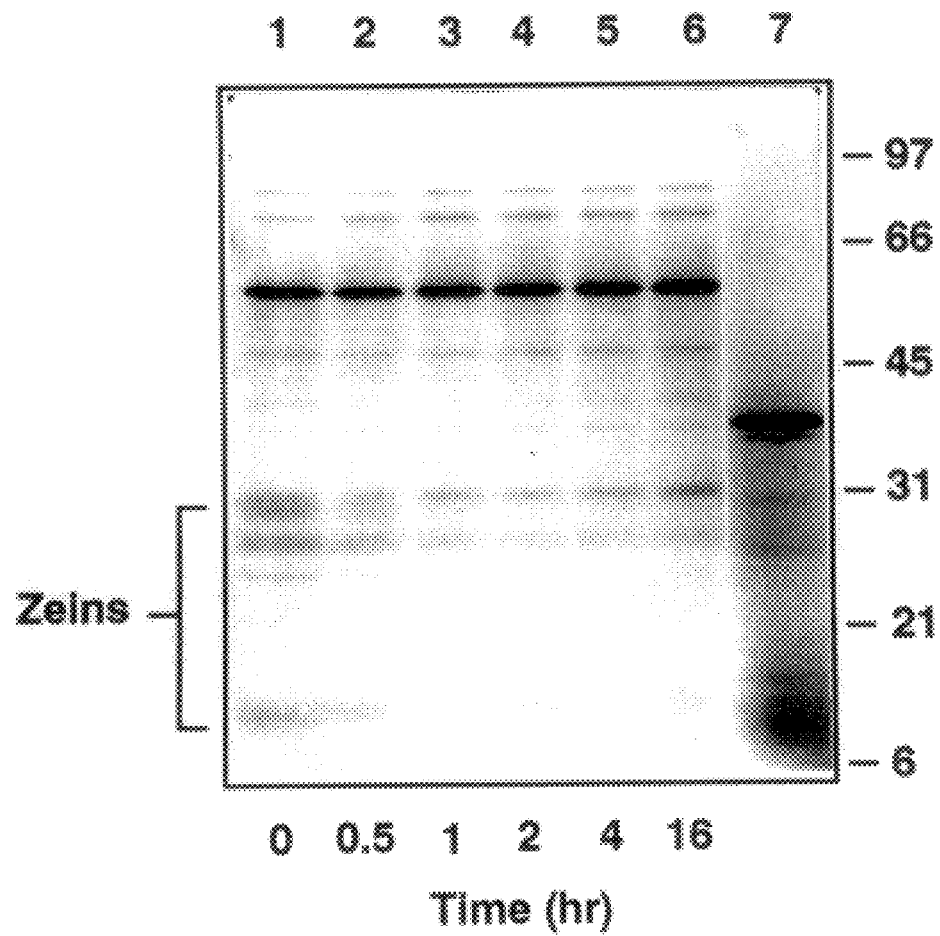
FIG. 4 Time Course of Zein Hydrolysis. Wet-milled starch granules were incubated in the absence (lane 1) or presence (lanes 2–6) of thermolysin at 2 μg mg$^{-1}$ with 5 mM CaCl$_2$. Proteins remaining associated with the starch granules were then extracted and analyzed by SDS-PAGE. Lane 7 contains proteins first extracted from gelatinized starch and were then subjected to thermolysin digestion for 30 minutes before loading onto gels. M denotes molecular mass markers.

The minimum incubation time required for the complete removal of surface-bound zeins at a thermolysin to granule ration of 2 μg per mg was determined (FIG. 4). Relative to controls with no thermolysin added (FIG. 4, lane 1), zein hydrolysis becomes evident after 30 minutes (FIG. 4, lane 2). As incubation times are extended, additional zein proteins are removed. When granules are incubated for 2 hours or longer, most of the zein proteins are effectively digested (FIG. 4, lanes 4–6). As observed previously, proteins larger than 30 kDa are unaffected by protease digestion unless granules are pre-gelatinized. Nevertheless, all the proteins extracted from the starch granule are intrinsically thermolysin-sensitive, since they are totally hydrolyzed by thermolysin after SDS extraction (FIG. 7, lane 7) (Mu-Forster et at. 1996). Based upon these findings, a 4 hour incubation period was used for subsequent characterization experiments.

Effect of pH.

Figure 5:
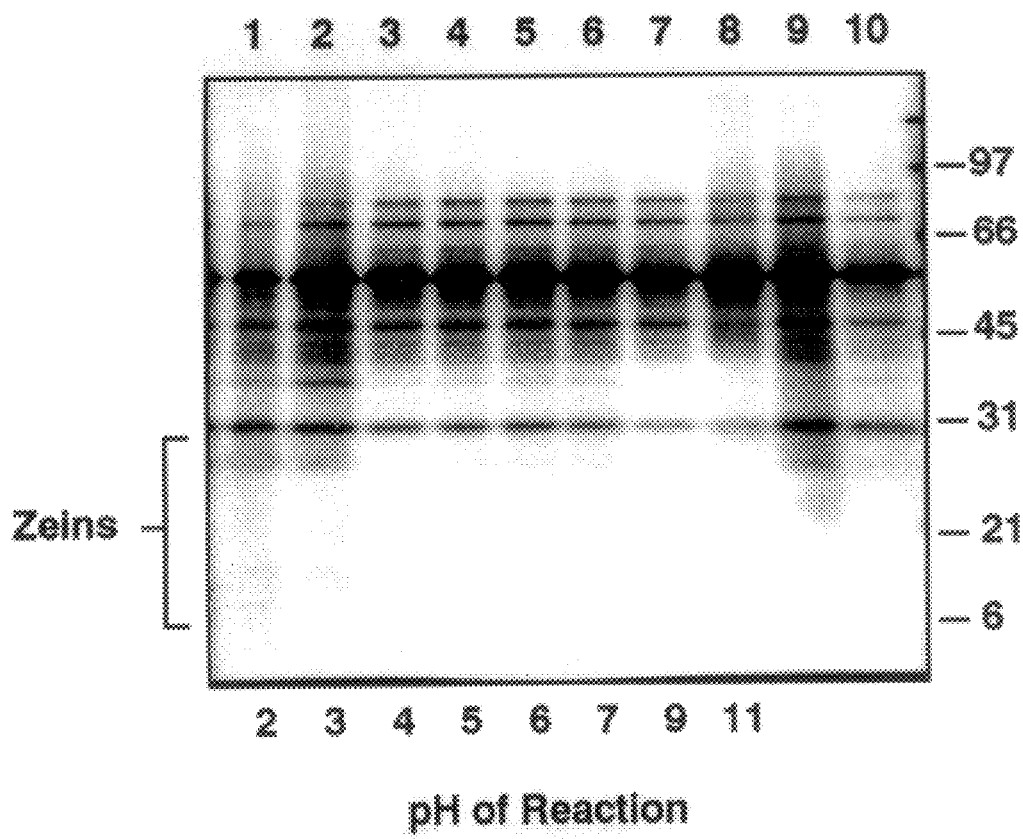
FIG. 5 Effect of pH on Zein Hydrolysis. Wet-milled starch granules suspended in steeping solution were incubated with thermolysin. pH values were adjusted as indicated (lanes 1–8). Lane 9 is a control with no thermolysin added. Lane 10 contains wet-milled starch granules washed with water 5 times before thermolysin treatment. Proteins remaining associated with the starch granules were then extracted and analyzed by SDS-PAGE. M denotes molecular mass markers.

The effect of pH on zein removal is shown in FIG. 5. In this experiment, the pH of wet-milled starch granules suspended in steeping solution was adjusted to values between 2 and 11, and samples were subjected to proteolysis. A silver stained gel shows that zeins are completely removed by thermolysin at pH values of 4 and above (FIG. 5, lanes 3–8). On the other hand, zeins were not hydrolyzed at pH 3 and below (FIG. 5, lanes 1 and 2). The two major steeping solution components, lactic acid and sulfur dioxide, do not appear to inhibit protease activity.

Effect of Calcium.

Since thermolysin has an absolute requirement for Ca$^{2+}$ (Feder et al 1971; Tajima et al. 1976), the effects of Ca$^{2+}$ on deproteinization were investigated. With laboratory prepared starch, thermolysin failed to exert its proteolytic effect in the absence of exogenous Ca$^{2+}$ (FIG. 6, lane 2). When Ca$^{2+}$ was increased to 0.5 mM or higher (FIG. 6, lanes 5–7), removal of zeins was achieved.

On the other hand, starch granules prepared by the industrial wet milling process did not require addition of exogenous Ca$^{2+}$. Full surface deproteinization occurred even in the absence of exogenous Ca$^{2+}$ (data not shown). This is probably due to use of hard water, which provides sufficient levels of Ca$^{2+}$ to activate thermolysin. To demonstrate this point, starch granules were washed with 200 mM EDTA to chelate divalent cations prior to incubation with thermolysin. Zein hydrolysis then became Ca$^{2+}$ dependent, with complete hydrolysis occurring at 0.5 mM (data not shown).

EXAMPLE 5

Starch Functionality

Pigmentation

Table 2 shows the effect of deproteinization on pooled color values of dry starch granules. Significantly lower "b" values, which indicate degree of yellowness (27.0% reduction) were observed in the deproteinized starch samples. Thermolysin-catalyzed zein removal also resulted in lower $H(°)_{ab}$ values which indicates the degree of hue (31% reduction). However, no significant changes in "a" (redness) and "L" (lightness) values were observed. These results indicate that starch granule deproteinization significantly enhances the color of starch preparations, which become significantly whiter in appearance. Conversion to a less yellow hue (decreased "b" and H(°)ab values) as the result of starch granule deproteinization may due to the fact that pigments which are non-covalently adsorbed to zeins during kernel disruption and steeping are released upon hydrolysis of granule surface proteins.

Table 2. Color Profiles of Untreated and Deproteinized Maize Starches.

Wet-milled starch granules were incubated with thermolysin at concentration of 0.4 $\mu$g mg$^{-1}$ in 5 mM $CaCl_2$. Hydrolysis was conducted at 64° C. for 4 hours Starch granules were washed five times with water to remove residual thermolysin and then air-dried. Control starch were treated parallel to deproteinized starch with thermolysin omitted.

| Color Values | Control Starch | Deproteinized Starch |
|---|---|---|
| L | 97.82 ± 0.03 | 98.34 ± 0.06 |
| a | −0.51 ± 0.02 | −0.54 ± 0.02 |
| b | 2.26 ± 0.01 | 1.65 ± 0.01 |
| $H(°)_{ab}$ | 4.43 ± 0.02 | 3.06 ± 0.02 |

Color values are the average of 8 measurements.

Starch Thermal and Pasting Properties.

Differential scanning calorimetry measurements were conducted to evaluate the thermal behavior of deproteinized starches (FIG. 7). Three samples were evaluated, and each exhibited a single thermal transition (gelatinization) profile. Whereas heat treatment alone increased gelatinization temperature (C vs. thermolysin control), deproteinization per se had no effect. In addition, zein removal did not markedly effect enthalpy values.

To determine the effect of zein removal on starch pasting properties, RVA analysis was conducted (FIG. 8). Starch granules were digested with thermolysin at 64° C. or 50° C. Samples incubated without thermolysin treatment served as controls. At 64° C., no difference was observed between treated samples and controls. At 50° C., deproteinized starch granules generated slightly higer cold paste viscosity than controls during the holding period after cooling relative to the parallel treated control. Compared to 50° C., heat treatment alone at 64° C. resulted in decreased peak viscosities and increased cold paste viscosities. The minimal effects of deproteinization on thermal and pasting properties demonstrates that the removal of zeins from starch granule surfaces by thermolysin does not alter starch granule integrity.

EXAMPLE 6

Removal of Zeins Using Thermolysin vs. L. Lactis Extracts

To establish whether other protease preparations were as effective as thermolysin in removing zeins from the surface of corn starch granules, a comparative study was undertaken wherein maize starch granules were treated with thermolysin or cell extracts of L. Lactis. These cell extracts were described in U.S. Pat. No. 5,246,718 (Haring et al. 1993) as having peptidase activity toward oligopeptides in starch. Cells of L. lactis were grown in Lactobacillus MRS both at 37° overnight. Cells were harvested by centrifugation at 5,000×g for 10 minutes, lysed with glass beads and by sonication, and cell extracts were recovered by centrifugation. Aminopeptidase activity of the cell extract was determined using L-Lue p-nitroanilide as substrate. Release of the p-nitronailine chromophore was measured spectrophotometrically at 400 nm. The cell extract used in this experiment contained a peptidase activity of 0.004 units/ml, which is four times higher than the lowest working activity described by the Haring et al. patent.

Enzymatic starch granule deproteinization was conducted in a 1 ml suspension containing 0.003 units of peptidase per 50 mg of starch, which falls within the suggested range of use. The reaction was carried out at 50° C. for 4 hours with or without calcium present, and was stopped by washing the starch granules five items with water. Equivalent samples were treated with thermolysin in parallel. Granule-associated proteins were then extracted and fractionated by SDS-PAGE. Gels were visualized by silver staining and western blotting using zein antibody.

Figure 10A:
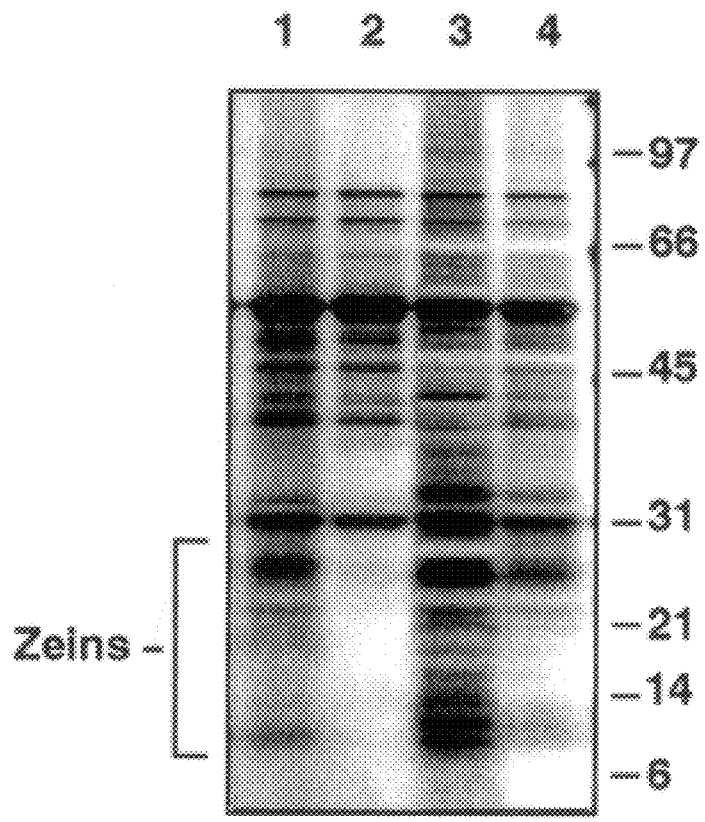
FIG. 10 Comparison of Zein Removal from Maize Starch Granules by Thermolysin and Cell Extracts of L. lactis. A. Silver stained gel. B. Immunoblot. Starch granules were incubated at 50° C. for 4 hours with thermolysin (lane 2), or with L. lactis cell extracts containing aminopeptidase (3×10$^6$ unit/mg) in the presence (lane 3) or absence (lane 4) of calcium. Lane 1 is a parallel control prepared without enzymes. Granules were washed five times with water, and remaining proteins were extracted. Proteins were separated by SDS-PAGE, and were stained with silver, or subjected to western blotting probed with δ-zein antibodies.
Figure 10B:
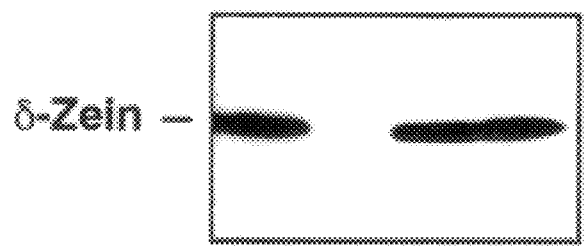

As shown in the previous examples, thermolysin treatment removed all of the lower molecular weight proteins from starch granules (FIG. 10A, lane 2). However, peptidase activity in the L. lactis cell extract had virtually no effect on zein removal, whether calcium was present or not (FIG. 10A, lanes 3 and 4). Furthermore, large amounts of soluble protein from the L. lactis cell extract bound to the starch granules and could not be removed by the five aqueous washings (FIG. 10A, lanes 3 and 4). Western blotting using the 10-kDa δ-zein antibody shows that thermolysin digestion completely removes δ-zein from starch granules (FIG. 10B, lane 2). However the L. lactis extract was not able to deplete starch granules of zein proteins (FIG. 10B, lanes 3, 4 vs. 1).

These results indicate that thermolysin treatment removes zeins from maize starch granules by a simple digestion step followed by aqueous washes. While Haring's method might effectively digest oligopeptides from potato starch granules using a L. Lactis cell extract in conjunction with physical purification steps (e.g. gas stripping or solvent extraction), it completely lacks the ability to hydrolyze larger proteins such as zeins from starch granules of maize.

Having described preferred embodiments of the invention with reference to the accompanying figures, it is to be understood that the invention is not limited to those precise embodiments, and that various changes and modifications may be effected therein by one skilled in the art without departing from the scope or spirit of the invention as defined in the appended claims.

The following references referred to in this document are hereby incorporated by reference:

REFERENCES

American Association of Cereal Chemists, 1983. Methods 44–19 and 46–13. In: *Approved Methods of the AACC*, 8th Ed, AACC, St. Paul, Minn.

Biss, R. and Cogan, U. 1996. Sulfur dioxide in acid environment facilitates corn steeping. *Cereal Chem.* 73:40–44.

Cline, K., Werner-Washburne, M., Andrews, J. and Keegstra, K. 1984. Thermolysin is a suitable protease for probing the surface of intact pea chloroplasts. *Plant Physiol.* 75:675–678.

Denyer, K., Dunlap, F, Thorbjornsen, T., Keeling, P. and Smith, A. M. 1996. The major form of ADP-glucose pyrophosphorylase in maize (*Zea mays* L.) endosperm is extra-plastidial. *Plant Physiol.* 112:779–785.

Eckhoff, S. R. and Tso, C. C. 1991. Starch recovery from steeped corn grits as affected by drying temperature and added commercial protease. *Cereal Chem.* 68:319–320.

Feder, J. Garrett, L. R. and Wildi, B. S. 1971. Studies on the role of calcium in thermolysin. *Biochemistry* 10:4552–4555.

Hamaker, B. R., Mohamed, A. A., Habben, J. E., Huang, C. P. and Larkins, B. A. 1995. Efficient procedure for extracting maize and sorghum kernel proteins reveals higher prolamin contents than the conventional method. *Cereal Chem.* 72:583–588.

Haring, P. G. M., De Kok, P. M. T., Potman, R. P., and Wesdorp, J. J., U.S. Pat. No. 5,246,718 (issued Sep. 21, 1993).

Hoseney, R. C. 1994. *Principles of Cereal Science and Technology,* Second Edition,:American Association of Cereal Chemists, St. Paul, Minn.

Keil, B. 1992. *Specificity of Proteolysis.* Springer-Verlag, Berlin Heidelberg. 336 pp.

Kreis, M., Shewry, Forde, B. G., Forde, J., and Miflin, B. J. 1985. Structure and evolution of seed storage proteins and their genes with particular reference to those of wheat, barley and rye. ., *Oxford Surveys of Plant Molecular & Cell Biology,* 2: 253–317.

Larkins, B. A., Pedersen, M., Marks, D. and Wilson, D. R. 1984. The zein proteins of maize endosperm. *Trends Biochem. Sci.* 9:306–308.

Kirihara, J. A. Humsperger, J. P., Mahoney, W. C. and Messing, J. W. 1988. Differential expression of a gene for a methionine-rich storage protein in maize. *Mol. Gen. Genet.* 211: 477–484.

Mu, C., Ham, C., Ko, YT., Singletary, G. W., Keeling, P. L. and Wasserman, B. P. 1994. Association of a 76 kDa polypeptide with soluble starch synthase I activity in maize (cv73) endosperm. *Plant J.* 6:151–159.

Mu-Forster, C., Huang, R., Powers, J. R., Harriman, R. W., Knight, M., Singletary, G. W., Keeling, P. L. and Wasserman, B. P. 1996. Physical association of starch biosynthetic enzymes with starch granules of maize endosperm. Granule-associated forms of starch synthase land starch branching enzyme II. *Plant Physiol.* 111:821–829.

Porzio, M. A. and Pearson, A. M. 1976. Improved resolution of myofibrillar proteins with sodium dodecyl sulfate-polyacrylamide gel electrophoresis. *Biochim. Biophys. Acta* 490:27–34.

Shotwell, M. A. and Larkins, B. A. 1989. *The Biochemistry and Molecular Biology of Seed Storage Proteins,* Academic Press, 297–345.

Skrede, G., Store Bakken, T. and Naes, T. 1990. Evaluation of color in raw, backed and smoked flesh of rainbow trout fed astaxanthin or canthaxanthin. *J Food Sci.* 55:1574–1578.

Steinke, J. D. and Johnson, L. A. 1991. Steeping maize in the presence of multiple enzymes. I. Static batchwise steeping. *Cereal Chem.* 68:7–12.

Steinke, J. D., Johnson, L. A. and Wang, C. 1991. Steeping maize in the presence of multiple enzymes. II. Continuous countercurrent steeping. *Cereal Chem.* 68:12–17.

Tajima, M., Urabe, l., Yutani, K. and Odada, H. 1976. Role of calcium ions in the thermostability of thermolysin and *Bacillus subtilis* var. *amylosacchariticus* neutral protease. *Eur. J Biochem.* 64:243–247.

Tkachuk, R., 1969, Nitrogen-to-protein conversions factors for cereals and oil seed meals. Cereal Chem 46: 419–423.

Towbin, H., Staehelin, T. and Gordon, J. 1979. Electrophoretic transfer of proteins from polyacrylamide gels to nitrocellulose sheets: procedure and some applications. *Proc. Natl. Acad. Sci. USA* 76:4350–4354.

Watson, S. A. 1984. Corn and Sorghum Starches: Production. In: *Starch: Chemistry and Technology,* edited by Whistler, R. L., BeMiller, J. N. and Paschall, E. F., Academic Press, Orlando, Fla., pp.433–442.

Wilson, C. M. 1987. Proteins of the Kernel. In: *Corn Chemistry and Technology,* edited by Watson, S. A. and Ramstad, P. E., American Association of Cereal Chemists, Inc., St. Paul, Minn., pp.273–310.

Wilson, C. M. 1991. Multiple zeins from maize endosperms characterized by reversed-phase high performance liquid chromatography. *Plant Physiol.* 95:777–786.

Xu, Q. and Chitnis, P. R. 1995. Organization of photosystem I polypeptides. *Plant Physiol.* 108:1067–1075.

We claim:

1. A method for purifying starch granules obtained from maize, comprising treating said starch granules with thermolysin at a sub-gelatinization temperature to selectively remove surface-associated proteins, including zein proteins from the surface of the starch granules.

2. The method according to claim 1, wherein the sub-gelatinization temperature is from about 20° C. to about 68° C.

3. A method of removing internalized proteins from starch granules obtained from maize, comprising treating the starch granules with thermolysin at a sufficient gelatinization temperature to remove the internalized protein from said starch granules.

4. The method according to claim 1, wherein the treatment of the starch granules with thermolysin is conducted at a pH of from about 2 to about 11.

5. The method according to claim 1, wherein the surface-associated proteins removed from the surface of the starch granules have a molecular weight of about 10 to about 30 kDa as measured by SDS-PAGE.

6. The method according to claim 1, wherein treatment of the starch granules with thermolysin is performed in a mixture containing calcium in a concentration of from about 0.5 mM to about 50 mM.

7. Purified starch granules obtained from maize, which have been treated with thermolysin and which are substantially free of surface-associated proteins otherwise found on the starch granule.

8. The purified starch granules according to claim 7 having the following characteristics:

a) being hypoallergenic relative to starch not treated with thermolysin: and b) having an improved flavor relative to starch not treated with thermolysin.

9. The purified starch granules according to claim 7, characterized as having reduced pigmentation relative to starch granules not treated with thermolysin.

10. The purified starch granules according to claim 7, wherein the starch granules have a protein content of from about 0.13 to about 0.14% relative to the protein content of 0.4 to 1.0% for starch not treated with thermolysin.

11. A starch product obtained from the process of claim 1.

12. A method of reducing pigmentation of starch from maize comprising treating maize during the steeping or post-steeping processes or isolated starch granules with thermolysin at a sub-gelatinization temperature to selectively remove surface-associated proteins from the surface of the starch granules.

13. The method according to claim 1, wherein the sub-gelatinization temperature is from about 50° C. to about 68° C.

14. The method according to claim 3, wherein the sub-gelatinization temperature is from about 50° C. to about 68° C.

* * * * *